United States Patent [19]

Weuthen

[11] Patent Number: 5,756,694

[45] Date of Patent: May 26, 1998

[54] PROCESS FOR THE PRODUCTION OF LIGHT-COLORED ALKYL AND/OR ALKENYL OLIGOGLYCOSIDES

[75] Inventor: Manfred Weuthen, Solingen, Germany

[73] Assignee: Henkel Kommanditgesellschaft auf Aktien, Duesseldorf, Germany

[21] Appl. No.: 553,482

[22] PCT Filed: May 9, 1994

[86] PCT No.: PCT/EP94/01484

§ 371 Date: Nov. 20, 1995

§ 102(e) Date: Nov. 20, 1995

[87] PCT Pub. No.: WO94/26757

PCT Pub. Date: Nov. 24, 1994

[30] Foreign Application Priority Data

May 18, 1993 [DE] Germany ............ 43 16 601.6

[51] Int. Cl.$^6$ .................. C07G 3/00; C07H 15/00; C07H 17/00
[52] U.S. Cl. ............... 536/18.5; 536/4.1; 536/18.6
[58] Field of Search ............... 536/18.5, 18.6, 536/1.11, 4.1; 8/111; 336/127; 252/351

[56] References Cited

U.S. PATENT DOCUMENTS

| | | | |
|---|---|---|---|
| 3,452,064 | 6/1969 | Stein et al. | 260/400 |
| 4,465,828 | 8/1984 | Rau et al. | 536/18.6 |
| 4,483,979 | 11/1984 | Mao | 536/18.6 |
| 4,557,729 | 12/1985 | McDaniel, Jr. et al. | 8/111 |
| 4,762,918 | 8/1988 | McDaniel, Jr. et al. | 336/127 |
| 4,898,934 | 2/1990 | Lueders et al. | 536/18.6 |
| 4,904,774 | 2/1990 | McDaniel, Jr. et al. | 336/127 |
| 4,990,605 | 2/1991 | Lueders | 536/18.5 |
| 5,003,057 | 3/1991 | McCurry et al. | 536/18.6 |
| 5,079,350 | 1/1992 | Fujita et al. | 536/18.6 |
| 5,104,981 | 4/1992 | Yamamuro et al. | 536/18.6 |
| 5,374,716 | 12/1994 | Biermann et al. | 536/18.6 |
| 5,538,669 | 7/1996 | Schulz et al. | 252/351 |
| 5,554,742 | 9/1996 | Wolf et al. | 536/18.6 |
| 5,576,425 | 11/1996 | Hill et al. | 536/18.6 |
| 5,612,467 | 3/1997 | Weuthen et al. | 536/18.6 |

FOREIGN PATENT DOCUMENTS

| | | |
|---|---|---|
| 0077167 | 10/1982 | European Pat. Off. |
| 0077167 | 4/1983 | European Pat. Off. |
| 0165721 | 5/1985 | European Pat. Off. |
| 0301298 | 7/1988 | European Pat. Off. |
| 0338151 | 10/1989 | European Pat. Off. |
| 0389753 | 1/1990 | European Pat. Off. |
| 0388857 | 9/1990 | European Pat. Off. |
| WO9003977 | 4/1990 | WIPO |
| WO9211270 | 7/1992 | WIPO |
| WO9322324 | 11/1993 | WIPO |

*Primary Examiner*—John Kight
*Assistant Examiner*—Dameron Jones
*Attorney, Agent, or Firm*—Wayne C. Jaeschke; John E. Drach; Henry E. Millson, Jr.

[57] ABSTRACT

Light-colored alkyl and/or alkenyl oligoglycosides corresponding to formula (I)

$$R^1O\text{---}[G]_p \qquad (I)$$

which $R^1$ is an alkyl and/or alkenyl radical containing 4 to 22 carbon atoms, G is a sugar unit containing 5 or 6 carbon atoms and p is a number of 1 to 10, can be produced by a process in which sugars are subjected to acid-catalyzed acetalization with a large excess of primary alcohols, the reaction mixture is neutralized in the presence of reducing agents and is then bleached in known manner. At the same time, the quality of the excess fatty alcohol to be separated off is considerably improved.

21 Claims, No Drawings

PROCESS FOR THE PRODUCTION OF LIGHT-COLORED ALKYL AND/OR ALKENYL OLIGOGLYCOSIDES

BACKGROUND OF THE INVENTION

1. Field of the Invention

This invention relates to a process for the production of light-colored alkyl and/or alkenyl oligoglycosides in which neutralization of the acidic catalysts is carried out in the presence of reducing agents.

2. Statement of Related Art

Alkyl oligoglycosides and, in particular, alkyl oligoglucosides are nonionic surfactants which are acquiring increasing significance by virtue of their excellent detergent properties and their high ecotoxicological compatibility. They are produced from sugars and starch degradation products which are normally acetalized in the presence of acidic catalysts. For reasons associated with the law of mass action, it is advisable to remove the water of condensation continuously from the reaction equilibrium and to use one component, usually the relatively inexpensive fatty alcohol, in an adequate excess. On completion of the reaction, the acidic catalyst is neutralized, for example with sodium hydroxide and/or magnesium oxide, and the excess fatty alcohol is distilled off to a residual content of <1% by weight.

The alkyl oligoglycosides obtained after distillation are heavily discolored and are unsuitable for marketing on aesthetic grounds. Accordingly, to produce light-colored products, the alkyl oligoglycosides have to be bleached after distillation. It is obvious in this connection that there is a considerable demand for processes which, even if they do not prevent it, at least limit the discoloration of the crude reaction products during their production. Accordingly, the problem is to produce lighter-colored products for the same quantity of bleaching agents or to obtain products of satisfactory color with, comparatively, a smaller quantity of bleaching agents.

Another problem affecting the production of alkyl oligoglycosides is the quality of the fatty alcohol which is recovered during the distillation step and returned to the process. In continuous operation, the distillate alcohol undergoes uncreasing discoloration accompanied by the accumulation of carbonyl compounds which necessitate separate working up. Here, too, it is desirable to carry out the process for the production of alkyl oligoglycosides in such a way that any deteriorations in quality can at least be limited if not completely avoided.

DESCRIPTION OF THE INVENTION

The present invention relates to a process for the production of alkyl and/or alkenyl oligoglycosides corresponding to formula (I)

$$R^1O\text{—}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10, by acid-catalyzed acetalization of sugars with primary alcohols, in which the reaction mixture is neutralized in the presence of reducing agents and then bleached in known manner.

It has surprisingly been found that the addition of reducing agents in the neutralization of the crude acetalization products after bleaching leads to products significantly improved in color. At the same time, the color and carbonyl value of the fatty alcohols recovered after distillation are improved to such an extent that there is no longer any need for separate working up, even after a large number of cycles.

Alkyl and/or alkenyl oligoglycosides

Alkyl and alkenyl oligoglycosides are known compounds which may be obtained by the relevant methods of preparative organic chemistry. EP-A1-0 301 298 and WO 90/3977 are cited as representative of the extensive literature available on the subject.

The alkyl and/or alkenyl oligoglycosides may be derived from aldoses or ketoses containing 5 or 6 carbon atoms, preferably from glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization below 1.7 and, more particularly, between 1.2 and 1.4 are preferred from the performance point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and technical mixtures thereof such as are obtained, for example, in the hydrogenation of technical fatty acid methyl esters or in the hydrogenation of aldehydes from Roelen's oxo synthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight $C_{12}$ alcohol as an impurity, and alkyl oligoglucosides based on technical $C_{9/11}$ oxoalcohols (DP=1 to 3) are preferred.

The alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil alcohol having a DP of 1 to 3 are preferred.

Reducing agents

In connection with surfactants, the use of reducing agents for improving quality is known from individual examples, although their addition during the neutralization step is new. For example, it is proposed in EP-B1 0 077 167 (Rohm & Haas) to carry out the acetalization of glucose in the presence of an acidic catalyst and a reducing agent. According to EP-B1 0 165 721 (Staley), light-colored alkyl oligoglycosides are obtained by treatment of the discolored products with a bleaching agent and an $SO_2$ source. The subject of EP-A1 0 338 151 (Henkel) is a process in which bleaching of the alkyl oligoglycosides is carried out in the presence of reducing agents, for example sodium boranate or Raney nickel. Finally EP 0 388 857 (Kao) relates to a process in which the crude reaction products are treated with boranates after neutralization of the acidic catalysts and the acidic catalysts are subsequently destroyed by addition of acids.

Although products more or less satisfactory in color can be obtained by the processes mentioned above, they do not have any effect on the quality of the excess fatty alcohol to be removed and are therefore unsatisfactory in terms of the complex problem addressed by the present invention.

Reducing agents suitable for use in the process according to the invention are, for example, complex hydrides, for example, lithium aluminium hydride, lithium aluminium tri-tert.butyloxyhydride, sodium borohydride, sodium dihydrido-bis-(2-methoxyethoxy)-aluminium, potassium borohydride and calcium borohydride;

hydrogen adsorbed on transition metals, for example Raney nickel, Raney cobalt, platinum black, palladium black, $H_2$/platinum on active carbon;

acids of phosphorus or alkali metal salts thereof in which the phosphorus has an oxidation number below 5, for example phosphorous acid, hypophosphorous acid, sodium hypophosphite;

acids of sulfur or alkali metal salts thereof in which the sulfur has an oxidation number below 6, for example sulfurous acid and sodium dithionite.

The reducing agents may typically be used in quantities of 0.5 to 5% by weight and preferably in quantities of 1 to 3% by weight, based on the glycose. In performance terms, it has proved to be of particular advantage to use 1 to 3% by weight sodium hypophosphite.

Acetalization

Production of the alkyl and/or alkenyl oligoglycosides by acetalization of sugar with fatty alcohols is known per se. Glucose and fatty alcohol are normally introduced first in a molar ratio of 1:2 to 1:8 and, after the addition of an acidic catalyst (for example p-toluene sulfonic acid or alkylbenzene sulfonic acid), are heated with continuous removal of the water of condensation until the residual glucose content in the reaction mixture is below 1% by weight, preferably below 0.5% by weight and more preferably below 0.05% by weight. The reaction products are then first neutralized by addition of the base, for example an alkali metal and/or alkaline earth metal oxide, hydroxide or carbonate, and the reducing agent and, finally, the excess alcohol is removed, for example in falling film and/or thin layer evaporators. Bleaching in the presence of bleach boosters and peroxide compounds and conversion of the products into pastes are carried out as final operations. Although the conditions under which and quantities with which the neutralization and bleaching of the alkyl and/or alkenyl oligoglycosides are carried out are not completely acritical, they may readily be gathered from the cited prior art by the expert without any need for inventive activity.

Industrial Applications

The alkyl and/or alkenyl oligoglycosides obtainable by the process according to the invention are particularly light-colored after bleaching. Accordingly, they are suitable for use in laundry detergents, dishwashing detergents and cleaning products and in hair-care and personal hygiene products in which they may be present in quantities of 1 to 50% by weight and preferably in quantities of 3 to 35% by weight, based on the particular product.

Another advantage is that the fatty alcohol recovered during distillation is not discolored and has such low carbonyl values that it may be returned to the process without working up.

The following Examples are intended to illustrate the invention without limiting it in any way.

EXAMPLES

Example 1

General procedure for the production of alkyl oligoglucosides 180 g (1 mol) glucose and 1160 g (5.8 mol) $C_{12-14}$ coconut oil fatty alcohol (Lorol® 1214, a product of Henkel KGaA, Düsseldorf/FRG) were introduced into a 2-liter three-necked flask equipped with a stirrer, dropping funnel and water separator and heated under reduced pressure (20 mbar) to a temperature of 110° C. 0.8 g (0.028 mmol) aqueous sulfosuccinic acid solution (70% by weight) were added through the dropping funnel. The water of reaction accumulating during the acetalization was continuously removed through the water separator and collected in a trap cooled with liquid nitrogen. The reaction was terminated after 7 h, by which time 18 ml water of reaction had accumulated. The residual glucose content of the reaction mixture was <0.1% by weight.

The reaction product was then neutralized (as in Examples 2 to 4 and Comparison Examples C1 and C2) and the excess fatty alcohol was removed under reduced pressure (1 mbar) and at a sump temperature of approx. 180° C. to a residual content of <1% by weight. The alkyl oligoglucoside remaining behind was made into a paste with water at 80° C. (solids content approx. 50% by weight), after which 500 ppm $Mg^{2+}$ ions (in the form of $MgSO_4.7H_2O$) were added. The color values were determined with a 5% by weight solution in water/isopropyl alcohol (1:1) in a Klett photometer (1 cm round cell).

Example 2

The alkyl oligoglucoside was produced in accordance with Example 1. Neutralization was carried out with 1.2 g sodium hydroxide in the form of a 50% by weight solution with addition of 3 g $NaH_2PO_2.H_2O$. The results are set out in Table 1.

Example 3

The alkyl oligoglucoside was produced in accordance with Example 1. However, the residual glucose content was 0.5% by weight. Neutralization was carried out with 2.2 g sodium hydroxide in the form of a 50% by weight solution with addition of 7 g $NaH_2PO_2.H_2O$. The results are set out in table 1.

Example 4

The alkyl oligoglucoside was produced in accordance with Example 1. However, the residual glucose content was 0.5% by weight. Neutralization was carried out with 2.2 g sodium hydroxide in the form of a 50% by weight solution with addition of 5 g $Na_2O_4S_2$. The results are set out in Table 1.

Comparison Example C1

The alkyl oligoglucoside was produced in accordance with Example 1. Neutralization was carried out with 1.2 g sodium hydroxide in the form of a 50% by weight solution. The results are set out in Table 1.

Comparison Example C2

The alkyl oligoglucoside was produced in accordance with Example 1. However, the residual glucose content was 0.5% by weight. Neutralization was carried out with 2.2 g sodium hydroxide in the form of a 50% by weight solution. The results are set out in Table 1.

TABLE 1

Test results

Color value paste (Klett)

| Example | A | B | C | Color FA | COV FA |
|---------|-----|-----|----|--------------|--------|
| 2 | 80 | 17 | — | Colorless | <0.1 |
| 3 | 90 | 22 | — | Colorless | 0.1 |
| 4 | 200 | 50 | — | Colorless | 0.2 |
| C1 | 500 | 90 | 28 | Light yellow | 0.6 |
| C2 | 500 | 140 | 30 | Yellow | 1.2 |

Legend:
A = Color of unbleached paste
B = Color after bleaching with 0.5% by weight $H_2O_2$
C = Color after bleaching with 1.5% by weight $H_2O_2$
FA = Fatty alcohol
COV = Carbonyl value

What is claimed is:

1. A process for the production of alkyl and/or alkenyl oligoglycosides corresponding to formula (I):

$$R^1O\text{—}(G)_p \qquad (I)$$

wherein $R^1$ is an alkyl and/or alkenyl radical containing 4 to 22 carbon atoms, G is a sugar unit containing 5 or 6 carbon atoms and p is a number from 1 to 10, wherein said process is comprised of the steps of:

(1) reacting a saturated or unsaturated primary alcohol having from 4 to 22 carbon atoms and a sugar having 5 or 6 carbon atoms in the presence of an acid catalyst;

(2) neutralizing the reaction mixture of step (1) in the presence of a reducing agent selected from the group consisting of: (a) an acid of phosphorus or alkali metal salt thereof in which the phosphorus has an oxidation number below 5, (b) an acid of sulfur or alkali metal salt thereof in which the sulfur has an oxidation number below 6, (c) a complex hydride, and (d) hydrogen adsorbed on a transition metal;

(3) removing excess saturated or unsaturated primary alcohol from the neutralized reaction mixture; and (4) bleaching the reaction mixture from step (3) containing the alkyl and/or alkenyl oligoglycoside of formula I.

2. The process of claim 1 wherein in formula I $R^1$ is a $C_{4-11}$ alkyl radical, and G is a glucose unit.

3. The process of claim 1 wherein in formula I $R^1$ is a $C_{12-22}$ alkyl radical, and G is a glucose unit.

4. The process of claim 1 wherein in step (2) the amount of said reducing agent is from about 0.5 to about 5% by weight based on the weight of the sugar.

5. The process of claim 1 wherein in step (1) water of condensation formed by the reaction is continuously removed from the reaction mixture.

6. The process of claim 1 wherein in formula I, p=1 to 6.

7. The process of claim 6 wherein p=1.1 to 3.0.

8. The process of claim 6 wherein p=1.2 to 1.4.

9. The process of claim 1 wherein in step (1) the primary alcohol is hydrogenated $C_{12/14}$ coconut oil alcohol.

10. The process of claim 1 wherein in step (1) the primary alcohol is at least one $C_8$ to $C_{10}$ alcohol or a technical $C_{9/11}$ oxoalcohol.

11. The process of claim 1 wherein in step (2) the reducing agent is a complex hydride.

12. The process of claim 1 wherein in step (2) the reducing agent is an acid of phosphorus or alkali metal salt thereof in which the phosphorus has an oxidation number below 5.

13. The process of claim 1 wherein in step (2) the reducing agent is an acid of sulfur or alkali metal salt thereof in which the sulfur has an oxidation number below 6.

14. The process of claim 1 wherein in step (2) the reducing agent is hydrogen adsorbed on a transition metal.

15. The process of claim 4 wherein the amount of reducing agent is from about 1 to about 3%.

16. The process of claim 12 wherein the reducing agent is sodium hypophosphite.

17. The process of claim 1 wherein in step (1) the molar ratio of sugar to alcohol is from about 1:2 to about 1:8.

18. The process of claim 1 wherein step (3) is carried out by distillation.

19. The process of claim 1 wherein step (1) is carried out until the sugar content in the reaction mixture is less than 1% by weight.

20. The process of claim 1 wherein in step (2) the neutralization is carried out by the addition of a base.

21. The process of claim 1 wherein in step (1) water of condensation formed by the reaction is continuously removed from the reaction mixture and the reaction is carried out until the sugar content in the mixture is less than about 0.5% by weight.

* * * * *